(12) United States Patent
Lee

(10) Patent No.: US 8,509,279 B2
(45) Date of Patent: Aug. 13, 2013

(54) SOLID DYE RESONATOR, AND SOLID DYE LASER HANDPIECE COMPRISING SAME

(75) Inventor: Hee Chul Lee, Gyeonggi-do (KR)

(73) Assignee: Lutronic Corporation, Gyeonggi-do (KR)

( * ) Notice: Subject to any disclaimer, the term of this patent is extended or adjusted under 35 U.S.C. 154(b) by 14 days.

(21) Appl. No.: 13/387,667

(22) PCT Filed: Jul. 27, 2010

(86) PCT No.: PCT/KR2010/004911
§ 371 (c)(1),
(2), (4) Date: Jan. 27, 2012

(87) PCT Pub. No.: WO2011/013978
PCT Pub. Date: Feb. 3, 2011

(65) Prior Publication Data
US 2012/0120979 A1    May 17, 2012

(30) Foreign Application Priority Data
Jul. 27, 2009   (KR) .................. 10-2009-0068287

(51) Int. Cl.
*H01S 3/20*    (2006.01)
(52) U.S. Cl.
USPC .................. 372/53; 372/9; 372/92; 372/107; 372/108
(58) Field of Classification Search
USPC .......................... 372/9, 53, 92, 107
See application file for complete search history.

(56) References Cited

U.S. PATENT DOCUMENTS

| | | | | |
|---|---|---|---|---|
| 4,727,552 A | * | 2/1988 | Porte et al. | 372/20 |
| 4,796,270 A | * | 1/1989 | Sheng et al. | 372/54 |
| 4,878,224 A | * | 10/1989 | Kuder et al. | 372/53 |

FOREIGN PATENT DOCUMENTS

| | | |
|---|---|---|
| JP | 06-021554 A | 1/1994 |
| KR | 10-0269028 B1 | 10/2000 |
| KR | 10-0425598 B1 | 4/2004 |
| KR | 20-0355632 Y1 | 7/2004 |

OTHER PUBLICATIONS

Korean Patent Abstracts, Publication No. 10-0269028, Registration Date Jul. 18, 2000, 2 pages.
Patent Abstracts of Japan, Publication No. 06-021554, dated Jan. 28, 1994, 1 page.
Korean Patent Abstracts, No. 1020010057948 A, dated Jul. 5, 2001 (corresponds to KR Publication No. 10-0425598), 2 pages.
International Search Report issued in PCT/KR2010/004911, mailed on Apr. 12, 2011, with translation, 4 pages.

* cited by examiner

*Primary Examiner* — Dung Nguyen
(74) *Attorney, Agent, or Firm* — Osha Liang LLP

(57) ABSTRACT

The present invention relates to a solid dye resonator, and to a solid dye laser hand piece comprising same. The solid dye resonator comprises: solid dye; a high-reflection mirror; an output coupler; a first mounting plate on which the high-reflection mirror is mounted; a second mounting plate which is spaced apart from the first mounting plate and which has a surface on which the output coupler is mounted; a driving motor mounted on the first mounting plate, such that a motor shaft is directed toward the second mounting plate; and a rotary shaft interposed between the first mounting plate and the second mounting plate, and connected to the motor shaft of the driving motor such that the rotary shaft interlockingly rotates with the rotation of the driving motor.

10 Claims, 4 Drawing Sheets

SOLID DYE RESONATOR, AND SOLID DYE LASER HANDPIECE COMPRISING SAME

TECHNICAL FIELD

The present invention relates to a solid dye resonator and, more particularly, to a solid dye resonator and a solid dye handpiece laser including the same, in which a solid dye is rotated by using a driving motor so that a position where pumping light is irradiated is varied (Le., the pumping light is made not to be continuously irradiated to one place), thereby being suitable for significantly extending the life span of a solid dye and increasing the pulse repetition rate.

BACKGROUND ART

In general, a solid dye is a laser oscillation medium solidified by injecting dye into plastic or glass in the existing liquid dye laser.

Here, the dye is not dye used in a common life, but is a specific dye enabling laser oscillation.

Furthermore, an apparatus in which a resonator employing the solid dye is included in the hand piece of a medical laser device is called a solid dye handpiece laser. That is, the solid dye handpiece laser is a laser reduced in size in a hand piece form by using the solid dye.

Here, the hand piece refers to a part grasped by the hand of an operator in order to adjust the direction of a laser beam in a medical laser.

For example, Utility Model Application No. 2003-0037805 entitled "solid dye handpiece laser" has been known as technology regarding the solid dye handpiece laser.

Conventional solid dye lasers, including Utility Model Application No. 2003-0037805 entitled "solid dye handpiece laser", however, had the following problems.

The input energy of lasers is not fully converted into output energy, and most of the amount of the input energy not converted is converted into heat and consumed.

A conventional solid dye laser was problematic in that the life span of a solid dye was short and the pulse repetition rate Hz was low because the solid dye had a cylindrical shape and pumping light incident on a solid dye medium was irradiated to an always fixed position (i.e., one place).

That is, in case of the conventional solid dye laser, if the conventional solid dye laser is used for a long time, a surface of the solid dye is damaged by heat or dyes within the solid dye are quickly broken because a position on which the pumping light is incident is always constant. Accordingly, the life span becomes short, and the repetition rate is low.

DISCLOSURE

Technical Problem

The present invention has been created keeping in mind the above problems occurring in the prior art, and an object of a solid dye resonator and a solid dye handpiece laser including the same according to the present invention is to provide a solid dye resonator and a solid dye handpiece laser including the same, which are suitable for:

First, significantly extending the life span of a solid dye and increasing the pulse repetition rate by rotating the solid dye using a driving motor so that a position where pumping light is irradiated is varied (i.e., the pumping light is made not to be continuously irradiated to one place), Second, facilitating rotational control by constructing a solid dye in a disk form instead of a conventional cylindrical form, and Third, further extending the life span of a solid dye and also further increasing the pulse repetition rate by controlling the rotation of a driving motor (i.e., a driving source for rotating the solid dye) according to a pulse repetition rate set by a user.

Technical Solution

To achieve the object, a solid dye resonator including a solid dye of a laser gain medium, a high-reflection mirror, and an output coupler according to the present invention includes a first mounting plate configured to have a first mounting groove for mounting the high-reflection mirror formed therein, a second mounting plate spaced apart from the first mounting plate and configured to have a second mounting groove for mounting the output coupler formed therein at a position corresponding to the first mounting groove, a rotary shaft provided between the first mounting plate and the second mounting plate, and rotation driving means configured to rotatably drive the rotary shaft, wherein the rotary shaft penetrates the center of the solid dye so that pumping light reflected from the high-reflection mirror and the output coupler passes through the inside of the solid dye, and thus the solid dye is rotated while operating in conjunction with the rotary shaft, so that a position where the pumping light incident on the solid dye through the high-reflection mirror is irradiated is varied.

Here, the solid dye is the laser gain medium for oscillating a laser wavelength by absorbing input pumping light. The high-reflection mirror is spaced apart from one side of the solid dye and configured to transmit the pumping light toward the solid dye and to reflect light oscillated from the solid dye. The output coupler is spaced apart from the other side of the solid dye in parallel at a position corresponding to the high-reflection mirror and configured to partially reflect and transmit the light oscillated from the solid dye. The rotation driving means is a driving motor and installed in the first mounting plate so that the motor shaft of the rotation driving means is directed toward the second mounting plate. The rotary shaft is provided between the first mounting plate and the second mounting plate, connected to the motor shaft of the driving motor, and rotated while operating in conjunction with the rotation of the driving motor.

To achieve the above object, a solid dye handpiece laser including the solid dye resonator according to the present invention includes the solid dye resonator and a hand piece body configured to have the solid dye resonator seated therein and grasped by an operator.

Advantageous Effects

The solid dye resonator and the solid dye handpiece laser including the same according to the present invention having the above construction have the following effects.

First, there is an effect that the life span of a solid dye can be significantly extended and the pulse repetition rate can be increased by rotating the solid dye using the driving motor so that a position where pumping light is irradiated is varied (i.e., the pumping light is made not to be continuously irradiated to one place).

Second, there is an effect that rotational control is facilitated by constructing a solid dye in a disk form instead of a conventional cylindrical form.

Third, there is an effect that the life span of a solid dye can be further extended and the pulse repetition rate can be further increased by controlling the rotation of the driving motor (i.e., a driving source for rotating the solid dye) according to a pulse repetition rate set by a user.

MODE FOR INVENTION

Preferred embodiments of a solid dye resonator and a solid dye handpiece laser including the same according to the present invention are described in detail on the basis of the accompanying drawings.

Figure 1:
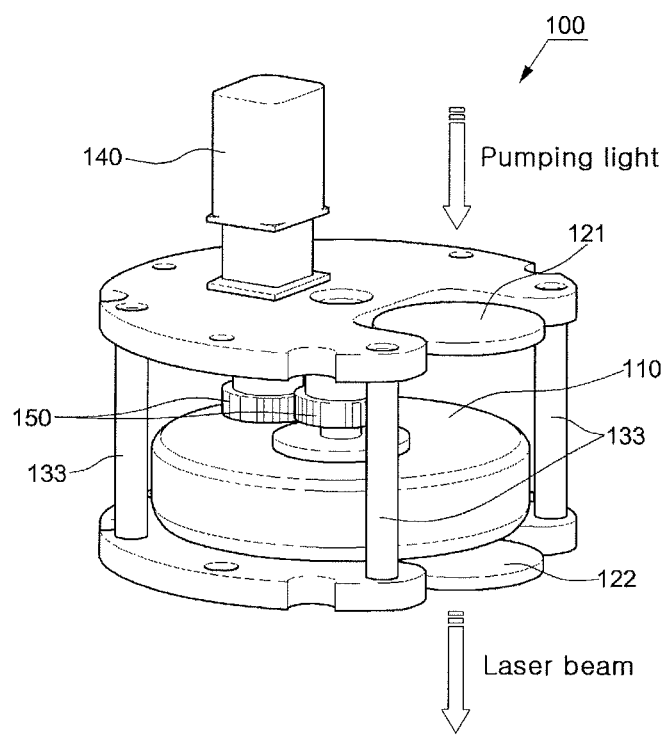
FIG. 1 is a perspective view of a solid dye resonator according to an embodiment of the present invention.
Figure 2:
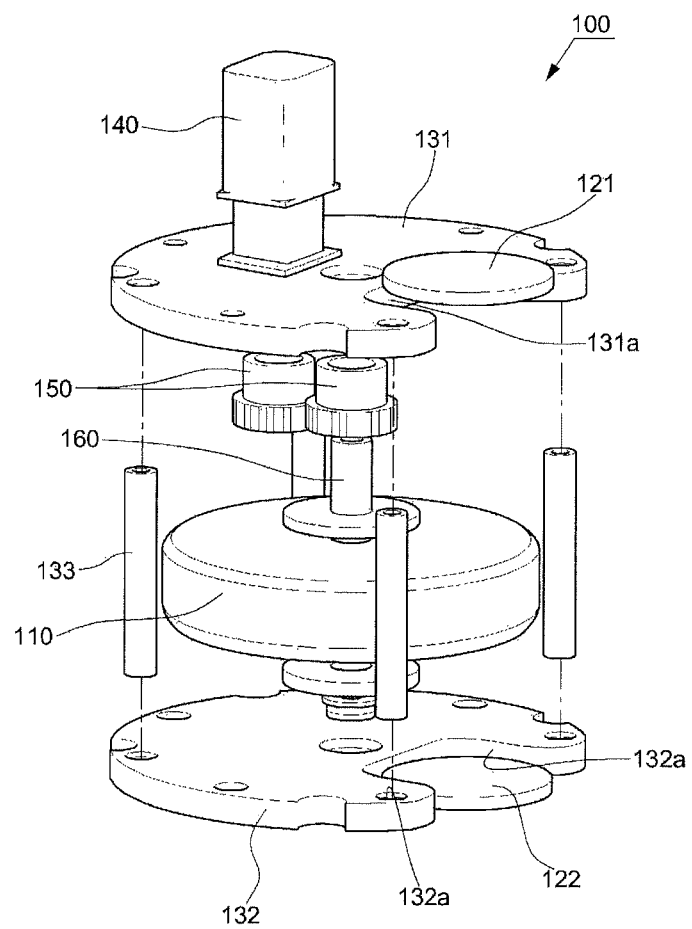
FIG. 2 is an exploded perspective view of FIG. 1.
Figure 3:
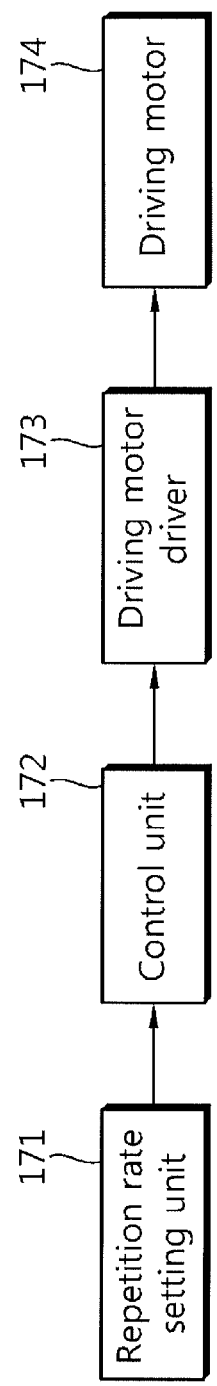
FIG. 3 is a block construction diagram for controlling a driving motor according to the pulse repetition rate in the solid dye resonator according to the embodiment of the present invention.

FIG. 1 is a perspective view of the solid dye resonator according to an embodiment of the present invention, FIG. 2 is an exploded perspective view of FIG. 1, and FIG. 3 is a block construction diagram for controlling a driving motor according to the pulse repetition rate in the solid dye resonator according to the embodiment of the present invention.

As shown in FIGS. 1 to 3, in the solid dye resonator 100 according to the embodiment of the present invention, including a solid dye 110 (i.e., a laser gain medium) configured to oscillate a laser wavelength by absorbing input pumping light, a high-reflection mirror 121 spaced apart from one side of the solid dye 110 and configured to transmit the pumping light toward the solid dye 110 and to reflect the light oscillated from the solid dye 110, and an output coupler 122 spaced apart from the other side of the solid dye 110 in parallel at a position corresponding to the high-reflection mirror 121 and configured to partially reflect and transmit the light oscillated from the solid dye 110, the solid dye resonator includes a first mounting plate 131 of a thin sheet shape configured to have a first mounting groove 131a for mounting the high-reflection mirror 121 formed therein, the high-reflection mirror 121 provided in the first mounting groove 131a of the first mounting plate 131, a second mounting plate 132 of a thin sheet shape spaced apart from the first mounting plate 131 and configured to have a second mounting groove 132a for mounting the output coupler 122 formed therein at a position corresponding to the first mounting groove 131a, the output coupler 122 provided in the second mounting groove 132a of the second mounting plate 132 so that the output coupler 122 faces the high-reflection mirror 121, a driving motor 140 installed in the first mounting plate 131 so that the motor shaft of the driving motor 140 is directed toward the second mounting plate 132 (i.e., the motor shaft is parallel to a length direction virtually connecting the first mounting plate 131 and the second mounting plate 132), a rotary shaft 160 provided between the first mounting plate 131 and the second mounting plate 132, connected to the motor shaft of the driving motor 140, and rotated while operating in conjunction with the rotation of the driving motor 140, and the solid dye 110 (i.e., a laser gain medium) configured to amplify and oscillate pumping light received after being transmitted by the high-reflection mirror 121. Here, the rotary shaft 160 penetrates the center of the solid dye 110 so that the pumping light reflected from the high-reflection mirror 121 and the output coupler 122 can pass through the inside of the solid dye 110, and thus the solid dye 110 is rotated while operating in conjunction with the rotary shaft 160. Accordingly, a position where the pumping light incident on the solid dye 110 through the high-reflection mirror 121 is irradiated is varied (i.e., the pumping light is made not to be continuously irradiated to any one place of the solid dye 110).

According to the above construction, a position where the pumping light is irradiated to the solid dye can be varied. Consequently, there are advantages in that the life span of the solid dye can be extended and the pulse repetition rate can be increased.

That is, the irradiation of the pumping light is not continuously concentrated on only one place because a position where the pumping light is irradiated to the solid dye can be changed. Accordingly, thermal damage to the solid dye 110 can be significantly reduced as compared with the prior art and the life span and the pulse repetition rate can be improved.

The high-reflection mirror 121 and the output coupler 122 may be provided in the first mounting groove 131a and the second mounting groove 132a, respectively, in various ways. For example, the high-reflection mirror 121 and the output coupler 122 may be detachably provided in the first mounting groove 131a and the second mounting groove 132a in a tight-fit way, may be adhered and fixed to the first mounting groove 131a and the second mounting groove 132a, or may be screwed onto and provided in the first mounting groove 131a and the second mounting groove 132a using screws.

The first mounting plate 131 and the second mounting plate 132 may be connected together and fixed by using a plurality of poles 133.

The solid dye resonator 100 according to the embodiment of the present invention is characterized in that it further includes power transfer means 150 between the motor shaft of the driving motor 140 and the rotary shaft 160 in order to smoothly transfer the rotation of the driving motor 140 to the rotary shaft 160.

The power transfer means 150 may include a plurality of reduction gears 150 which are installed in the driving motor 140 and the rotary shaft 160 and configured to transfer the rotation of the driving motor 140 to the rotary shaft 160.

In the solid dye resonator 100 according to the embodiment of the present invention, the solid dye 110 may be formed to have a disk form having a thickness d1.

According to the above construction, there are advantages in that the volume of the product can be reduced and rotational control is facilitated.

The solid dye resonator 100 according to the embodiment of the present invention further includes a repetition rate setting unit 171 for setting a pulse repetition rate Hz, a control unit 172 for calculating the rotational frequency of the driving motor 140 on the basis of the repetition rate Hz received from the repetition rate setting unit 171 and outputting the calculated rotational frequency of the driving motor 140 in the form of a rotational frequency control signal, and a driving motor driver 173 for controlling the driving and rotation of the driving motor 140 in response to the rotational frequency control signal received from the control unit 172.

When the rotation of the driving motor (i.e., a driving source for rotating the solid dye) is controlled according to a pulse repetition rate set by a user as described above, there are advantages in that the life span of the solid dye can be further extended and the pulse repetition rate can also be further increased.

Figure 4:
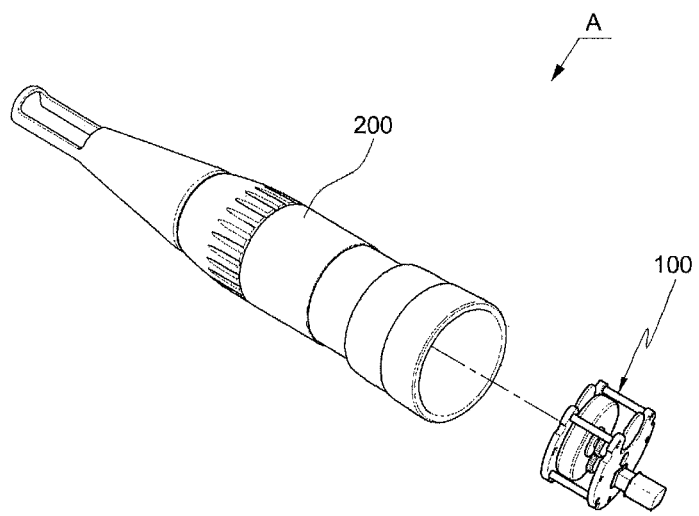
FIG. 4 is an exploded perspective view of a solid dye handpiece laser including the solid dye resonator according to an embodiment of the present invention.

FIG. 4 is an exploded perspective view of a solid dye handpiece laser including the solid dye resonator according to an embodiment of the present invention.

As shown in FIG. 4, the solid dye handpiece laser A including the solid dye resonator according to the embodiment of the present invention is characterized in that it includes the solid dye resonator 100 and a hand piece body 200 configured to have the solid dye resonator 100 seated therein and grasped by an operator.

The solid dye handpiece laser A including the solid dye resonator according to the embodiment of the present invention shown in FIG. 4 is characterized in that the solid dye resonator 100 is seated in the hand piece body 200 to form a hand piece type laser.

Meanwhile, the solid dye resonator 100 may be seated within the hand piece body 200 in various ways. For example, the entire solid dye resonator 100 may be seated within the hand piece body 200 by mounting the first mounting plate 131 and the second mounting plate 132 on the hand piece body 200.

Furthermore, the solid dye handpiece laser A including the solid dye resonator according to the embodiment of the present invention may be mounted on the articulated arm of, for example, a Q-switched Nd:YAG laser and used to obtain a laser having a different wavelength from pumping light.

For example, in the case in which the pumping light has a 532 nm wavelength, if the high-reflection mirror 121 is coated to transmit light of 532 nm and to reflect pieces of light of 585 nm and 650 nm and the output coupler 122 is coated to reflect light of 532 nm and to reflect part of pieces of light of 585 nm and 650 nm, but transmit part of the pieces of light of 585 nm and 650 nm, an outputted laser beam may have a wavelength of 585 nm or 650 nm.

An operational process of the solid dye resonator constructed as above and the solid dye handpiece laser including the same according to the present invention is described below.

Pumping light incident on the solid dye 110 through the high-reflection mirror 121 is converted into a laser pulse amplified in the solid dye 110 while being repeatedly reflected between the high-reflection mirror 121 and the output coupler 122 and is then outputted through the output coupler 122.

Furthermore, when the driving motor 140 is rotated by a specific rotational frequency, the solid dye 110 is also rotated. Accordingly, the pumping light is incident on a position different from a part on which the pumping light was first incident and continuously reflected between the output coupler 122 and the high-reflection mirror 121, so that an amplified laser pulse is outputted.

Meanwhile, the rotation of the driving motor 140 may be automatically controlled. For example, the rotation of the driving motor 140 may be controlled on the basis of a set pulse repetition rate.

That is, thermal damage to the solid dye can be further reduced by making fast the rotation of the motor when the pulse repetition rate is high and making slow the rotation of the motor when the pulse repetition rate is low.

The embodiment of the present invention is only an embodiment of the technical spirit of the present invention, and a person having ordinary skill in the art may modify the present invention in various ways within the technical spirit of the present invention.

The invention claimed is:

1. A solid dye resonator including a solid dye of a laser gain medium, a high-reflection mirror, and an output coupler, the solid dye resonator comprising:
a first mounting plate configured to have a first mounting groove for mounting the high-reflection mirror;
a second mounting plate spaced apart from the first mounting plate and configured to have a second mounting groove for mounting the output coupler at a position corresponding to the first mounting groove;
a rotary shaft provided between the first mounting plate and the second mounting plate; and
rotation driving means configured to rotatably drive the rotary shaft,
wherein the rotary shaft penetrates a center of the solid dye so that pumping light reflected from the high-reflection mirror and the output coupler passes through an inside of the solid dye, and thus the solid dye is rotated while operating in conjunction with the rotary shaft, so that a position where the pumping light incident on the solid dye through the high-reflection mirror is irradiated is varied.

2. The solid dye resonator of claim 1, wherein:
the rotation driving means is a driving motor, and
the solid dye resonator further comprises power transfer means between a motor shaft of the driving motor and the rotary shaft in order to smoothly transfer a rotation of the driving motor to the rotary shaft.

3. The solid dye resonator of claim 2, wherein the power transfer means include a plurality of reduction gears which are installed in the driving motor and the rotary shaft and configured to transfer the rotation of the driving motor to the rotary shaft.

4. The solid dye resonator of claim 3, wherein the solid dye is constructed in a disk form.

5. The solid dye resonator of claim 1, wherein:
the rotation driving means is a driving motor, and
the rotation driving means further comprises a repetition rate setting unit for setting a pulse repetition rate Hz; a control unit for calculating a rotational frequency of the driving motor based on the repetition rate Hz received from the repetition rate setting unit and outputting the calculated rotational frequency of the driving motor in a form of a rotational frequency control signal; and a driving motor driver for controlling the driving and rotation of the driving motor in response to the rotational frequency control signal received from the control unit.

6. A solid dye handpiece laser comprising:
a solid dye resonator including a solid dye of a laser gain medium, a high-reflection mirror, and an output coupler, the solid dye resonator comprising:
a first mounting plate configured to have a first mounting groove for mounting the high-reflection mirror;
a second mounting plate spaced apart from the first mounting plate and configured to have a second mounting groove for mounting the output coupler at a position corresponding to the first mounting groove;
a rotary shaft provided between the first mounting plate and the second mounting plate; and
rotation driving means configured to rotatably drive the rotary shaft,
wherein the rotary shaft penetrates a center of the solid dye so that pumping light reflected from the high-reflection mirror and the output coupler passes through an inside of the solid dye, and thus the solid dye is rotated while operating in conjunction with the rotary shaft, so that a position where the pumping light incident on the solid dye through the high-reflection mirror is irradiated is varied; and
a hand piece body configured to have the solid dye resonator seated therein and grasped by an operator.

7. The solid dye handpiece laser of claim 6, wherein the rotation driving means is a driving motor, and the solid dye resonator further comprises power transfer means between a motor shaft of the driving motor and the rotary shaft in order to smoothly transfer a rotation of the driving motor to the rotary shaft.

8. The solid dye handpiece laser of claim 7 wherein the power transfer means include a plurality of reduction gears which are installed in the driving motor and the rotary shaft and configured to transfer the rotation of the driving motor to the rotary shaft.

9. The solid dye handpiece laser of claim 8 wherein the solid dye is constructed in a disk form.

10. The solid dye handpiece laser of claim 6 wherein the rotation driving means is a driving motor, and the rotation driving means further comprises a repetition rate setting unit for setting a pulse repetition rate Hz; a control unit for calculating a rotational frequency of the driving motor based on the repetition rate Hz received from the repetition rate setting unit and outputting the calculated rotational frequency of the driving motor in a form of a rotational frequency control signal; and a driving motor driver for controlling the driving and rotation of the driving motor in response to the rotational frequency control signal received from the control unit.

\* \* \* \* \*